(12) United States Patent
Groenhagen et al.

(10) Patent No.: US 10,489,553 B2
(45) Date of Patent: Nov. 26, 2019

(54) CLINICAL DOCUMENT QUALITY REVIEW

(71) Applicant: CERNER INNOVATION, INC., Kansas City, KS (US)

(72) Inventors: Andrea Lorenzo Groenhagen, Lawrence, KS (US); Beth Elaine McCauley, Stillwell, KS (US); Jeffrey Scott Doyel, Shawnee, KS (US)

(73) Assignee: CERNER INNOVATION, INC., Kansas City, KS (US)

( * ) Notice: Subject to any disclaimer, the term of this patent is extended or adjusted under 35 U.S.C. 154(b) by 822 days.

(21) Appl. No.: 14/980,864

(22) Filed: Dec. 28, 2015

(65) Prior Publication Data

US 2016/0117455 A1 Apr. 28, 2016

Related U.S. Application Data

(63) Continuation-in-part of application No. 14/258,755, filed on Apr. 22, 2014.

(51) Int. Cl.
| | |
|---|---|
| *G06F 19/00* | (2018.01) |
| *G16H 40/20* | (2018.01) |
| *G16H 50/70* | (2018.01) |
| *G16H 50/20* | (2018.01) |

(52) U.S. Cl.
CPC .......... *G06F 19/328* (2013.01); *G16H 40/20* (2018.01); *G16H 50/20* (2018.01); *G16H 50/70* (2018.01)

(58) Field of Classification Search
CPC ...... G06F 19/328; G16H 40/20; G16H 50/20; G16H 50/70
See application file for complete search history.

(56) References Cited

U.S. PATENT DOCUMENTS

| | | | |
|---|---|---|---|
| 5,307,262 A | 4/1994 | Ertel | |
| 5,970,463 A | 10/1999 | Cave | |
| 2003/0083903 A1* | 5/2003 | Myers | G06F 19/324 705/2 |

(Continued)

OTHER PUBLICATIONS

Final Office Action dated Mar. 2, 2017 in U.S. Appl. No. 14/258,755, 14 pages.

(Continued)

*Primary Examiner* — Linh Giang Le
(74) *Attorney, Agent, or Firm* — Shook, Hardy & Bacon L.L.P.

(57) ABSTRACT

Computerized systems and methods identify deficiencies in patient data that may impact payment for services rendered to a patient and facilitates collection/correction of patient data to address the deficiencies. The deficiencies occur in two main situations: (1) a physician has confirmed a diagnosis that impacts payment but the patient data does not satisfy clinical evidence, direct evidence, and treatment requirements to support the diagnosis; and (2) the patient data satisfies clinical evidence, direct evidence, and treatment requirements to support a diagnosis but a physician has not confirmed the diagnosis. When a deficiency is identified, an electronic notice is generated and delivered over a communication network to a clinician computing device. The notice may provide the clinician access to a user interface that allows the clinician to enter additional information or clarify information in the patient data to address the deficiency.

20 Claims, 6 Drawing Sheets

(56) References Cited

U.S. PATENT DOCUMENTS

2004/0172297 A1* 9/2004 Rao ................. G06F 19/328
 705/2
2008/0052128 A1* 2/2008 Beraja ............... G06F 19/325
 705/3

OTHER PUBLICATIONS

First Action Interview Office Action and Examiner-Initiated Interview Summary dated Sep. 28, 2016 in U.S. Appl. No. 14/258,755, 5 pages.
First Action Interview Pilot Program Pre-Interview Communication dated Apr. 27, 2016 in U.S. Appl. No. 14/258,755, 5 pages.

* cited by examiner

| DIAGNOSIS ⎫302 | CLINICAL EVIDENCE REQUIREMENT(S) ⎫304 | DIRECT EVIDENCE REQUIREMENT(S) ⎫306 | TREATMENT REQUIREMENTS ⎫310 |
|---|---|---|---|
| ACUTE SYSTOLIC CONGESITVE HEART FAILURE | SHORTNESS OF BREATH; OR HISTORY OF CARDIOMYOPATHY | BNP > 200 | DIURETIC MEDICATION PRESCRIBED |
| ⋮ | ⋮ | ⋮ | ⋮ |
| ⋮ | ⋮ | ⋮ | ⋮ |
| ⋮ | ⋮ | ⋮ | ⋮ |
| ⋮ | ⋮ | ⋮ | ⋮ |

CLINICAL DOCUMENT QUALITY REVIEW

RELATED APPLICATION

This patent application is a continuation-in-part of U.S. application Ser. No. 14/258,755, filed Apr. 22, 2014, which is incorporated herein by reference in the entirety.

BACKGROUND

Under the Medicare program, inpatient medical services are bundled into a number of Diagnosis Related Groups. Hospitals are reimbursed for medical services rendered to patients on per-case flat rate based on the DRG identified for each case. There is a select group of diagnoses that have the potential to impact the DRG used to determine the payment to a hospital. Claims submitted by a hospital for payment may be audited (e.g., RAC Audits). The audits may focus on the diagnoses that impact the DRG payment to determine if the patient data submitted supports the diagnoses. If it is found that a diagnosis is not supported, the DRG payment could potentially be reduced and the hospital would have to pay back the difference.

BRIEF SUMMARY

Embodiments of the present invention relate to computerized systems and methods to identify deficiencies in patient data that may impact payment for services rendered to a patient and facilitates collection/correction of patient data to address the deficiencies. The deficiencies can occur in two main situations: (1) a physician has confirmed a diagnosis that impacts payment but the patient data does not satisfy clinical evidence, direct evidence, and treatment requirements to support the diagnosis; and (2) the patient data satisfies clinical evidence, direct evidence, and treatment requirements to support a diagnosis but a physician has not confirmed the diagnosis. When a deficiency is identified, an electronic notice is generated and delivered over a communication network to a clinician computing device. The notice may provide the clinician access to a user interface that allows the clinician to enter additional information or clarify information in the patient data to address the deficiency.

Accordingly, in one aspect, an embodiment of the present invention is directed to a method in a clinical computing environment. The method includes providing an application for installation on a clinician computing device associated with a clinician. The method also includes accessing patient data from an electronic medical record for a patient; determining whether any of a plurality of diagnoses that impact payment for medical services rendered for the patient are confirmed by a physician in the patient data; and determining whether clinical evidence, direct evidence, and treatment requirements for any of the plurality of diagnoses are satisfied by the patient data. If a first diagnosis has been confirmed by the physician but at least one of the clinical evidence, direct evidence, and treatment requirements for the first diagnosis is not satisfied by the patient data, the method include generating a first electronic message providing a reverse quality check notification, and transmitting the first electronic message over a communication network to the clinician computing device associated with the clinician, wherein the first electronic message causes the application to display the reverse quality check notification on the clinician computing device. If the clinical evidence, direct evidence, and treatment requirements for a second diagnosis are satisfied by the patient data but the second diagnosis has not been confirmed by the physician, the method includes generating a second electronic message providing a confirmation quality check notification, and transmitting the second electronic message over the communication network to the clinician computing device associated with the clinician, wherein the second electronic message causes the application to display the confirmation quality check notification on the clinician computing device.

In another embodiment, an aspect is directed to one or more computer storage media storing computer-useable instructions that, when used by one or more computing devices, cause the one or more computing devices to perform operations. The operations include identifying, from electronic medical data storing patient data for a patient, a diagnosis that impacts payment for medical services rendered for the patient. The operations also include accessing a data store storing requirements to support the diagnosis, and determining, from the data store, clinical evidence, direct evidence, and treatment requirements to support the diagnosis. The operations further include determining that at least one of the clinical evidence, direct evidence, and treatment requirements to support the diagnosis is not present in the patient data. The operations still further include generating an electronic message by inserting, into the electronic message, at least a portion of the patient data and information identifying that at least one of the clinical evidence, direct evidence, and treatment requirements to support the diagnosis that is not present in the patient data; and providing the electronic message, over a communication network, to a device associated with a clinician.

A further embodiment is directed to a system comprising: one or more processors; and one or more computer storage media storing instructions that, when used by the one or more processors, cause the one or more processors to: access electronic medical data storing patient data for a patient; access clinical evidence, direct evidence, and treatment requirements to support each of a plurality of diagnoses that impact payment for rendered medical services; determine that the patient data supports clinical evidence, direct evidence, and treatment requirements for a first diagnosis that impacts payment for medical services rendered for the patient but a physician treating the clinician has not confirmed the first diagnosis for the patient; generate an electronic message that includes at least a portion of the patient data and information indicating that the clinical evidence, direct evidence, and treatment requirements for the first diagnosis are supported by the patient data but the clinician has not confirmed the diagnosis for the patient; and provide the electronic message, over a communication network to a device associated with a clinician.

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

BRIEF DESCRIPTION OF THE SEVERAL VIEWS OF THE DRAWINGS

The present invention is described in detail below with reference to the attached drawing figures, wherein:

FIG. 3 is diagram showing a table storing clinic evidence, direct evidence, and treatment requirements for diagnoses in accordance with an embodiment of the present invention;

DETAILED DESCRIPTION

Figure 1:
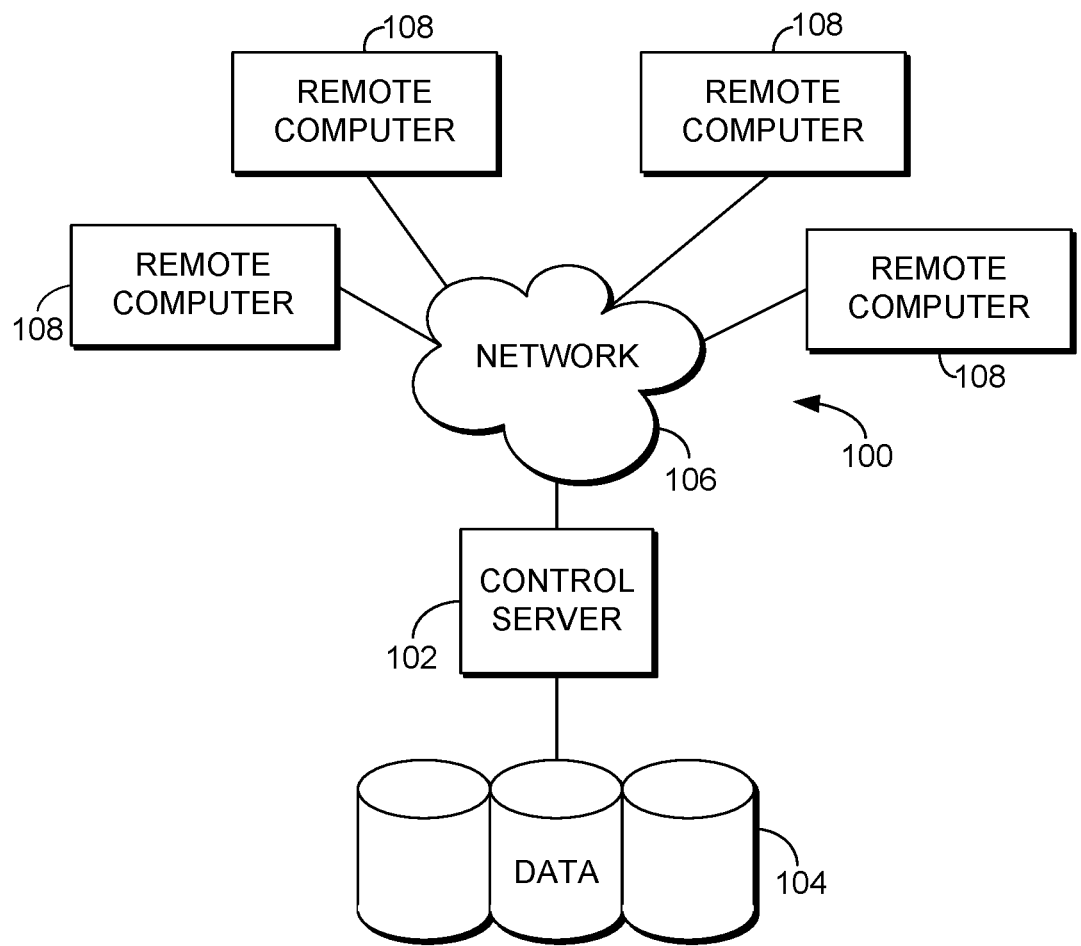
FIG. 1 is a block diagram of an exemplary computing environment suitable for use in implementing the present invention.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different components of methods employed, the terms should not be interpreted as implying any particular order among or between various steps herein disclosed unless and except when the order of individual steps is explicitly described.

Embodiments of the present invention provide computerized methods and systems that may be employed by hospitals to enable providers to create accurate and complete documentation of inpatient services rendered to patients thereby enabling both good quality of care over time and appropriate billing for the services rendered. This may include, for instance, DRG-based payments made by the Centers for Medicare and Medicaid Services (CMS). In particular, the computerized methods and systems, among other things, identify deficiencies in clinical documentation that may impact payments for services rendered to patients. The deficiencies may fall into one of two main situations. The first situation occurs when a physician documents a diagnosis that definitely confirms the condition ("confirmation") but one or more clinical indicator requirements for the diagnosis are not satisfied. This is referred to herein as a "reverse quality check." The second situation occurs when the clinical indicator requirements for a diagnosis are satisfied but a physician has not documented the diagnosis. This is referred to herein as a "confirmation quality check." As used herein, the term "clinical indicator" refers to any measure, observation, medical order, treatment plan, or other piece of patient data that may be used to determine the accuracy of a diagnosis for a patient.

Embodiments of the present invention provide a common approach applicable to any number of different diagnoses. By using a common approach, the same process can be used for all diagnoses, thereby making more efficient use of computer and networking resources. In particular, three categories of clinical indicator requirements are established for each diagnosis. These three categories of clinical indicator requirements include: clinical evidence requirements; direct evidence requirements; and treatment requirements. Clinical evidence comprises signs and symptoms that indicate the possible presence of a condition corresponding with a particular diagnosis. Direct evidence comprises objective data (e.g., lab work) that confirms with greater certainty the presence of a condition corresponding with a particular diagnosis. A treatment comprises actions performed for a patient to treat a particular condition.

For a given patient, the system is configured to analyze patient data to determine if a diagnosis that impacts payments has been identified. Additionally, the system is configured to analyze the patient data to determine if clinical evidence, direct evidence, and treatment requirements are all satisfied for any of a number of different categories. A notice is generated if: (1) a diagnosis has been identified in the patient data but the patient data does not support the clinical evidence, direct evidence, and treatment requirements for the diagnosis; or (2) the clinical evidence, direct evidence, and treatment requirements for a diagnosis are satisfied by the patient data by the physician has not confirmed the diagnosis in the patient data.

The system is also configured to facilitate the collection of data to support diagnoses in instances of reverse quality checks and to facilitate the confirmation of diagnoses in instances of confirmation quality checks. In particular, whenever a deficiency is identified by the system (e.g., missing diagnosis or missing clinical indicator requirement for an entered diagnosis), a notice is provided to a clinician regarding the deficiency. The notice can facilitate a clinician entering information to address the deficiency. In some embodiments, the notice comprises a user interface that allows a clinician to enter or clarify information. In other embodiments, the notice includes a hyperlink to allow the clinician to access a user interface to address the deficiency. For instance, the hyperlink may allow the clinician to access the patient's electronic medical record to enter/clarify information.

By providing a system that automatically analyzes the clinical documentation, looks for the possible deficiencies or points that need further clarification, and provides notices to clinicians that allow the clinicians to address the deficiencies, embodiments allow for the billing process to be automated and streamlined. Embodiments help create a more accurate diagnosis and provide a downstream impact of a more accurate DRG and more accurate billing claim. Embodiments efficiently use computer and network resources as only a single notice is needed to be sent to a clinician and a single access by the clinician to address a deficiency. This is in contrast to previous solutions that may require multiple electronic messages among multiple clinicians, rejections during audits, and other inefficiencies. In fact, automation can allow for a notice to be provided to a clinician immediately at the point in time he/she is signing the document. Providing this immediate feedback provide multiple benefits including greater clinical accuracy, eliminating the need to return at a later time to correct the document, lowering the cost to the organization, and improving the reimbursement levels for the organization.

As a specific example to illustrate an embodiment of the present invention, suppose a patient is admitted to a hospital with coronary artery disease. The doctor indicates in his progress notes that the patient has acute systolic congestive heart failure. The patient is noted to have shortness of breath and history of cardiomyopathy ("clinical evidence"). Laboratory work indicates the BNP (B-type natriuretic peptide) is 75 ("direct evidence"). The physician is restricting the patient's fluids and has ordered monitoring input and output. Acute systolic congestive heart failure has also been added as a diagnosis to the discharge summary by the physician.

If acute systolic congestive heart failure was coded and added to the claim being submitted to CMS for payment, the diagnosis would be a counted as a Major Complication/Comorbidity and increase the DRG payment. In accordance with an embodiment of the present invention, the system would identify that the acute systolic congestive heart failure diagnosis is one that impacts payment for the services rendered to the patient. Additionally, the system would analyze the patient data for the patient to determine if clinical evidence, direct evidence, and treatment requirements for the diagnosis are supported.

Suppose in the present example: the clinical evidence requirements for this diagnosis includes shortness of breath and/or a history of cardiomyopathy; the direct evidence requirement for this diagnosis is a BNP greater than 200; and the treatment requirement for the diagnosis is prescription of a diuretic medication. Accordingly, the clinical evidence from the patient data supports the clinical evidence requirement. However, the patient data does not support the direct evidence and treatment requirements. As such, the system alerts a Clinical Documentation Improvement (CDI) specialist (e.g., a person who is responsible for ensuring that claims being submitted to a payment provider have the necessary documentation) and/or the physician that the clinical indicator requirements are not satisfied for the diagnosis. The notice may indicate that the BNP is not elevated and the patient is not being treated with a diuretic. The physician would need to add documentation to justify the diagnosis or modify the diagnosis to coincide with the clinical indicators.

In a similar situation, suppose a patient is admitted with coronary artery disease. The physician indicates in his progress notes that the patient has shortness of breath and history of cardiomyopathy ("clinical evidence"). Laboratory work indicates the BNP is 250 ("direct evidence"). The physician prescribes a diuretic medication of Bumetanide ("treatment").

When the patient is discharged, the discharge summary makes no mention of acute systolic congestive heart failure, but only mentions "unspecified hypertensive heart disease." If acute systolic congestive heart failure had been documented then the claim would use a DRG that is more accurate.

In this situation, the system would see that all three categories (clinical evidence, direct evidence, treatment) are satisfied for a diagnosis of acute systolic congestive heart failure; however, there is no "confirmation" of the diagnosis by the physician. This would alert a CDI specialist and/or the physician that the "confirming" diagnosis is missing. The physician would need to add documentation to clarify the diagnosis or include a more precise diagnosis.

Referring to the drawings in general, and initially to FIG. 1 in particular, an exemplary computing system environment, for instance, a medical information computing system, on which embodiments of the present invention may be implemented is illustrated and designated generally as reference numeral 100. It will be understood and appreciated by those of ordinary skill in the art that the illustrated medical information computing system environment 100 is merely an example of one suitable computing environment and is not intended to suggest any limitation as to the scope of use or functionality of the invention. Neither should the medical information computing system environment 100 be interpreted as having any dependency or requirement relating to any single component or combination of components illustrated therein.

The present invention may be operational with numerous other general purpose or special purpose computing system environments or configurations. Examples of well-known computing systems, environments, and/or configurations that may be suitable for use with the present invention include, by way of example only, personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

The present invention may be described in the general context of computer-executable instructions, such as program modules, being executed by a computer. Generally, program modules include, but are not limited to, routines, programs, objects, components, and data structures that perform particular tasks or implement particular abstract data types. The present invention may also be practiced in distributed computing environments where tasks are performed by remote processing devices that are linked through a communications network. In a distributed computing environment, program modules may be located in local and/or remote computer storage media including, by way of example only, memory storage devices.

With continued reference to FIG. 1, the exemplary medical information computing system environment 100 includes a general purpose computing device in the form of a server 102. Components of the server 102 may include, without limitation, a processing unit, internal system memory, and a suitable system bus for coupling various system components, including database cluster 104, with the server 102. The system bus may be any of several types of bus structures, including a memory bus or memory controller, a peripheral bus, and a local bus, using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The server 102 typically includes, or has access to, a variety of computer readable media, for instance, database cluster 104. Computer readable media can be any available media that may be accessed by server 102, and includes volatile and nonvolatile media, as well as removable and non-removable media. By way of example, and not limitation, computer readable media may include computer storage media and communication media. Computer storage media may include, without limitation, volatile and nonvolatile media, as well as removable and nonremovable media implemented in any method or technology for storage of information, such as computer readable instructions, data structures, program modules, or other data. In this regard, computer storage media may include, but is not limited to, RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the server 102. Computer storage media does not comprise signals per se. Communication media typically embodies computer readable instructions, data structures, program modules, or other data in a modulated data signal, such as a carrier wave or other transport mechanism, and may include any information delivery media. As used herein, the term "modulated data signal" refers to a signal that has one or more of its attributes set or changed in such a manner as to encode information in the signal. By way of example, and not limitation, communication media includes wired media such as a wired network or direct-wired connection, and wireless media such as acoustic, RF, infrared, and other wireless media. Combinations of any of the above also may be included within the scope of computer readable media.

The computer storage media discussed above and illustrated in FIG. 1, including database cluster 104, provide storage of computer readable instructions, data structures, program modules, and other data for the server 102.

The server 102 may operate in a computer network 106 using logical connections to one or more remote computers 108. Remote computers 108 may be located at a variety of locations in a medical or research environment, for example, but not limited to, clinical laboratories, hospitals and other inpatient settings, veterinary environments, ambulatory settings, medical billing and financial offices, hospital administration settings, home health care environments, and clinicians' offices. Clinicians may include, but are not limited to, a treating physician or physicians, specialists such as surgeons, radiologists, cardiologists, and oncologists, emergency medical technicians, physicians' assistants, nurse practitioners, nurses, nurses' aides, pharmacists, dieticians, microbiologists, laboratory experts, genetic counselors, researchers, veterinarians, students, CDI specialists, and the like. The remote computers 108 may also be physically located in non-traditional medical care environments so that the entire health care community may be capable of integration on the network. The remote computers 108 may be personal computers, servers, routers, network PCs, peer devices, other common network nodes, or the like, and may include some or all of the components described above in relation to the server 102. The devices can be personal digital assistants or other like devices.

Exemplary computer networks 106 may include, without limitation, local area networks (LANs) and/or wide area networks (WANs). Such networking environments are commonplace in offices, enterprise-wide computer networks, intranets, and the Internet. When utilized in a WAN networking environment, the server 102 may include a modem or other means for establishing communications over the WAN, such as the Internet. In a networked environment, program modules or portions thereof may be stored in the server 102, in the database cluster 104, or on any of the remote computers 108. For example, and not by way of limitation, various application programs may reside on the memory associated with any one or more of the remote computers 108. It will be appreciated by those of ordinary skill in the art that the network connections shown are exemplary and other means of establishing a communications link between the computers (e.g., server 102 and remote computers 108) may be utilized.

In operation, a user may enter commands and information into the server 102 or convey the commands and information to the server 102 via one or more of the remote computers 108 through input devices, such as a keyboard, a pointing device (commonly referred to as a mouse), a trackball, or a touch pad. Other input devices may include, without limitation, microphones, satellite dishes, scanners, or the like. Commands and information may also be sent directly from a remote healthcare device to the server 102. In addition to a monitor, the server 102 and/or remote computers 108 may include other peripheral output devices, such as speakers and a printer.

Although many other internal components of the server 102 and the remote computers 108 are not shown, those of ordinary skill in the art will appreciate that such components and their interconnection are well known. Accordingly, additional details concerning the internal construction of the server 102 and the remote computers 108 are not further disclosed herein.

Figure 2:
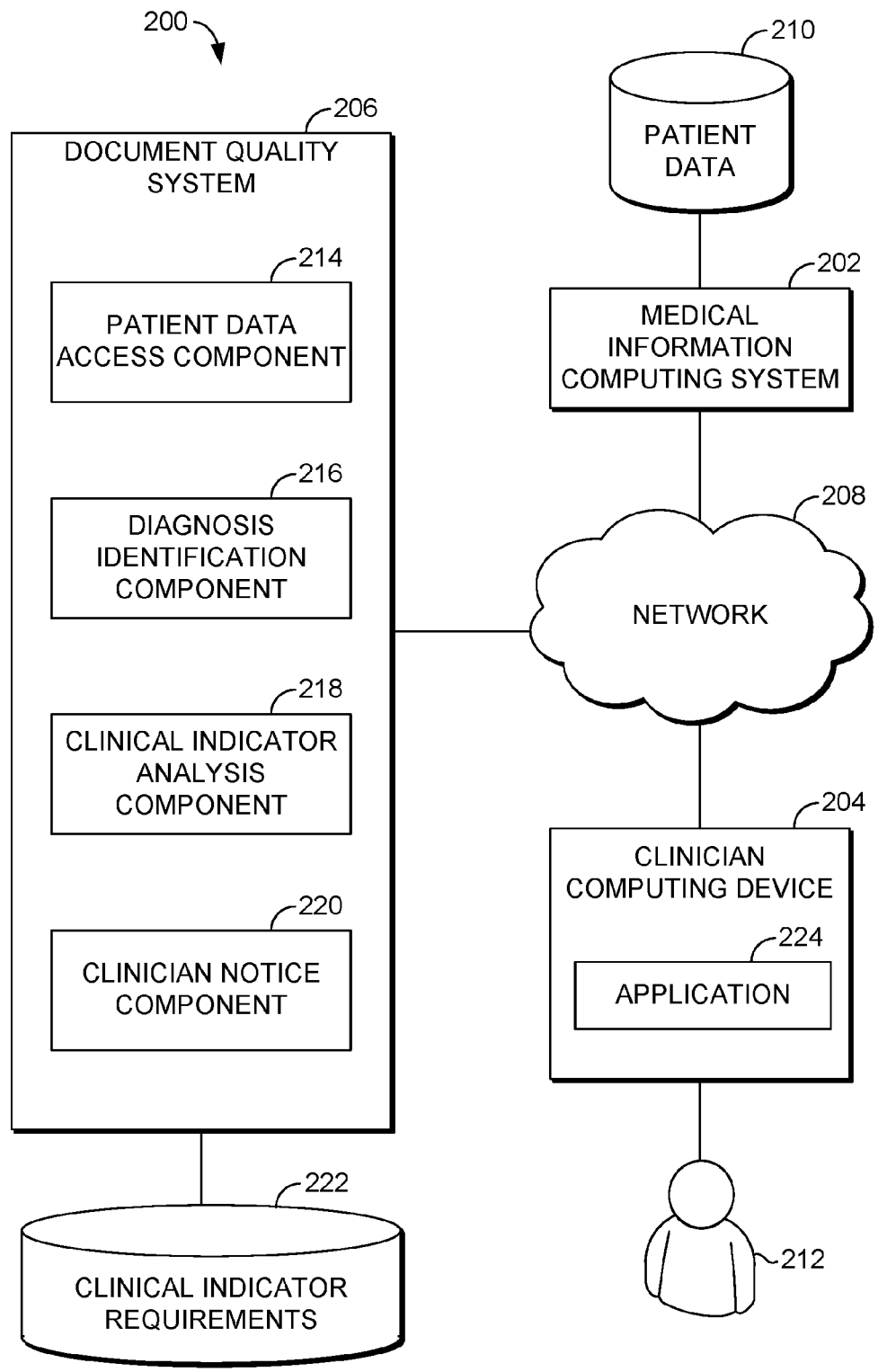
FIG. 2 is a block diagram of an exemplary system architecture in which embodiments of the invention may be employed.

Referring now to FIG. 2, a block diagram is provided illustrating an exemplary system 200 in which a document quality system 206 is generally configured to facilitate ensuring document quality for diagnoses, as well as the process of billing payment providers for services rendered to patients by a hospital and its clinicians. In accordance with embodiments of the present invention, the document quality system 206 is configured to perform reverse quality checks by recognizing when diagnoses that impact payment for services rendered to patients are not supported by clinical indicators and to perform confirmation quality checks by recognizing when clinical indicators support diagnoses but the diagnoses have not been confirmed by a physician. The document quality system 206 is also configured to facilitate the collection of data to support the diagnoses in instances of reverse quality checks and to facilitate the confirmation of diagnoses in instances of confirmation quality checks.

The document quality system 206 may be a stand-alone system interfaced with a medical information computing system 202 via a network 208 in accordance with one embodiment of the present invention, as shown in FIG. 2. The medical information computing system 202 may be a comprehensive computing system within a clinical environment similar to the exemplary computing system 100 discussed above with reference to FIG. 1. Although the document quality system 206 is shown separate from the medical information computing system 202 in FIG. 2, in some embodiments, the document quality system 206 may be a subsystem of the medical information computing system 202. Any and all such variations are contemplated to be within the scope of embodiments of the present invention.

As shown in FIG. 2, the document quality system 206 includes a patient data access component 214, diagnosis identification component 216, clinical indicator analysis component 218, a clinician notice component 220, and a clinical indicator requirements data store 222. The patient data access component 214 may generally be configured to access patient data 210 maintained by the medical information computing system 202 for billing purposes discussed herein.

The diagnosis identification component 216 operates to identify the presence or absence of diagnoses in patient data that will impact payments for services rendered to patients. In some embodiments, the document quality system 206 may maintain a list of diagnoses that impact payments. For instance, the list of diagnoses may include diagnoses that impact the DRG for a case. The diagnosis identification component 216 may employ the list of diagnoses to identify patient data that includes any of the listed diagnoses.

The clinical indicator analysis component 218 is configured to analyze patient data available for the patient to determine whether the patient data includes the clinical evidence requirements (i.e., clinical evidence, direct evidence, and treatment requirements) to support a diagnosis. The clinical indicator analysis component 218 may employ information regarding clinical indicator requirements for diagnoses stored in a clinical indicator requirements data store 222.

The clinical indicator requirements data store 222 can store information regarding clinical indicator requirements for diagnoses in any of a number of different manners in accordance with embodiments of the present invention. For instance, in some embodiments, the clinical indicator requirements data store 222 stores clinical indicator requirements indexed by diagnosis, such that the clinical indicator requirements data store 222 is searchable by diagnosis to retrieve the clinical evidence, direct evidence, and treatment requirements for a given diagnosis. For instance, FIG. 3 illustrates a table 300 storing clinical indicator requirements on a per diagnosis basis. As shown in FIG. 3, each row in the table 300 corresponds with a diagnosis 302. Additionally, the table 300 stores, for each diagnosis, clinical evidence requirement(s) 304, direct evidence requirement(s) 306, and treatment requirement(s). As an example, the first entry is for the diagnosis, acute systolic congestive heart failure. The clinical indicator requirements for this diagnosis include: (1) clinical evidence requirement of shortness of breath and/or history of cardiomyopathy; (2) direct evidence requirement of BNP>200; and (3) treatment requirement of a diuretic medication prescribed. The specific information for other diagnoses is not shown in FIG. 3 for clarity purposes.

The clinical indicator analysis component 218 can employ a data structure indexed by diagnosis (such as the table 300 of FIG. 3) to determine whether the clinical evidence, direct evidence, and treatment requirements for a diagnosis are supported by patient data for a patient. In such embodiments, the clinical indicator analysis component 218 retrieves the clinical evidence, direct evidence, and treatment requirements for a given diagnosis from the data structure. The clinical analysis component 218 then analyzes the patient data for the patient to determine whether the patient data supports the clinical evidence, direct evidence, and treatment requirements for that diagnosis. In the context of a reverse quality check, the diagnosis identification component 216 may first identify a diagnosis in the patient data for the patient, and the clinical indicator analysis component 218 may then search the data structure to identify the clinical evidence, direct evidence, and treatment requirements for that diagnosis and analyze the patient data in view of those clinical indicator requirements. In the context of a confirmation quality check, the clinical indicator analysis component 218 may iterate through each of the diagnoses. For each diagnosis, the clinical evidence, direct evidence, and treatment requirements are identified from the data structure, and the patient data is analyzed to determine whether the clinical indicator requirements for the diagnosis are supported.

In some embodiments, information is stored by the clinical indicator requirements data store 222 that is indexed by clinical evidence requirements, direct evidence requirements, and/or treatment requirements. For instance, a data structure may be indexed by clinical evidence requirements that stores one or more diagnoses that correspond with each of a number of different clinical evidence requirements. Similarly, a second data structure may be indexed by direct evidence requirements that stores one or more diagnoses that correspond with each of a number of different direct evidence requirements, and a third data structure may be indexed by treatment requirements that stores one or more diagnoses that correspond with each of a number of different treatment requirements. In such embodiments, the clinical indicator analysis component 218 analyzes patient data for the patient to categorize pieces of patient data as clinical evidence, direct evidence, and treatments. The clinical indicator analysis component 218 then: (1) searches the clinical evidence data structure based on the identified clinical evidence to determine which diagnoses are supported by clinical evidence from the patient data; (2) searches the direct evidence data structure based on the identified direct evidence to determine which diagnoses are supported by direct evidence from the patient data; and (3) searches the treatments data structure based on the identified treatments to determine which diagnoses are supported by treatments from the patient data. The clinical indicator analysis component 218 may then determine if the clinical evidence, direct evidence, and treatment requirements are supported for any diagnosis.

In still further embodiments, a tree-like graph or model may be employed to store information regarding clinical evidence, direct evidence, and treatment requirements for diagnoses that may be used by the clinical indicator analysis component 218 to identify whether diagnoses are supported by patient data. The tree-like graph or model may store clinical evidence, direct evidence, and/or treatment requirements at each node with a diagnosis at each leaf node. In such embodiments, patient data is initially analyzed to categorize different pieces of patient data into clinical evidence, direct evidence, and treatments. The clinical evidence, direct evidence, and treatments identified from the patient data are then used to traverse the tree-like graph or model until it is determined whether a leaf-node with a particular diagnosis is reached.

It should be understood that the above-described approaches for storing information regarding the clinical evidence, direct evidence, and treatment requirements for diagnoses have been provided by way of example only and not limitation. Other approaches for storing clinical indicator requirements for diagnoses and using the information to identify whether the requirements for diagnoses are supported by patient data may be employed in various embodiments of the present invention. Any and all such combinations and variations thereof are contemplated to be within the scope of embodiments.

In some embodiments, the clinical indicator analysis component 218 also analyzes patient data to identify disqualifying evidence and/or supportive evidence. Disqualifying evidence comprises information that disqualifies the possible presence of a condition corresponding with a particular diagnosis. If disqualifying evidence for a particular diagnosis is present in patient data, that diagnosis cannot be confirmed. For instance, a conflicting diagnosis may have been confirmed by the physician. If disqualifying evidence is identified when the clinical indicator requirements for a diagnosis are satisfied, a notice will not be generated since the disqualifying evidence would eliminate the need for the notice.

Supportive evidence comprises information that helps provide context to a clinician when confirming a condition associated with a particular diagnosis. While supportive evidence is not used in some embodiments to determine whether clinical indicator requirements are satisfied for a diagnosis, the supportive evidence may be collected and provided to a clinician when a notice is generated and sent to a clinician in the event of some deficiency in clinical indicators and/or confirmation of a diagnosis.

The diagnosis identification component 216 can be configured to identify diagnoses that impact payments in patient data and the clinical indicator analysis component 218 can be configured to identify whether diagnoses are supported by patient data at a variety of different points in time in various embodiments of the present invention. In some embodiments, the diagnosis identification component 216 identifies a diagnosis that impacts payment and the clinical indicator analysis component 218 identifies whether diagnoses are supported by patient data when a claim is being prepared for submission to a payment provider, such as the CMS. In other embodiments, the identifications occur at an earlier point in time. For instance, in some embodiments, the analyses are performed at the time a diagnosis or other patient data is entered for a patient. In other embodiments, the diagnosis identification component 216 and the clinical indicator analysis component 218 are configured to periodically (e.g., daily) scan patient data. Any and all such combinations and variations thereof are contemplated to be within the scope of embodiments of the present invention.

The clinician notice component 220 is configured to generate a notice to a clinician in instances when diagnoses entered by physicians are not supported by clinical indicators (i.e., reverse quality checks) and instances when clinical indicators support diagnoses but the diagnoses have not been confirmed by a physician (i.e., confirmation quality check). The clinician notice component 220 may deliver a notice to a clinician computing device, such as the clinician computing device 204 operated by the clinician 212.

A generated notice is provided to one or more clinicians. In some instances, a hospital has a CDI specialist who is responsible for ensuring that claims being submitted to a payment provider have the necessary documentation. The notice could be provided to the CDI specialist who may work with a treating physician to collect patient data to provide the missing clinical indicators. In some instances, the notice is provided to a physician or other clinician treating the patient. In some embodiments, a clinician may be selected to receive the notice based on the type of clinical indicator requirement missing. For instance, if data for a particular clinical indicator is usually provided by a particular type of clinician, the notice may be provided to that type of clinician.

The notice is an electronic message that is provided to the clinician computing device 204 over the network 208 using any electronic communication approaches, such as, for instance, an email, a text message, or a voice message to name a few. In some embodiments, the clinician computing device 204 includes an application 224 that provides a user interface for providing a notice for reverse quality checks and/or confirmation quality checks. For instance, the application 224 on the clinician computing device 204 may provide a queue of notices for reverse quality checks and/or confirmation quality checks. This queue may provide a clinician, such as a CDI specialist or physician, with a location to manage cases in which a diagnosis is not supported by the patient data and/or the patient data supports a diagnosis that has not been confirmed by a physician. For instance, a CDI specialist may be tasked with following up with other clinicians to collect patient data for missing clinical indicators and/or missing diagnoses.

The notice provided by the clinician notice component 220 may provide a range of different information and options. For reverse quality checks, in some embodiments, the notice simply indicates that a diagnosis that impacts quality and/or payments was identified as being confirmed by a physician but all clinical indicators required to support the diagnosis have not been found in available patient data. In other embodiments, the notice identifies which clinical indicators are missing from the patient data. In some embodiments, the notice identifies clinical indicators that were found in the patient data. In further embodiments, the notice identifies particular data that is needed to satisfy the missing clinical indicators or other actions that may be taken to collect the needed data. In some embodiments, the notice provides a user interface to collect, from a clinician, additional information or clarifying information that is added to the patient data to facilitate billing. The user interface may be a part of the notice itself or accessed from a hyperlink in the notice. In further embodiments, the notice includes one or more hyperlinks to perform specific actions (e.g., submit orders for tests) to collect needed data. Accordingly, the notice may prompt a clinician to perform additional actions to collect data needed to show clinical indicators required to support a diagnosis are present.

For confirmation quality checks, in some embodiments, the notice indicates that the quality indicator requirements for a diagnosis that impacts payment were identified, but the diagnosis has not been confirmed by a clinician. The notice may include or exclude information regarding the clinical evidence, direct evidence, and treatments from the patient data used to determine the clinical indicator requirements for the diagnosis are supported. In some embodiments, the notice provides a user interface to collect, from a clinician, a confirmation of a diagnosis and/or other information. The user interface may be a part of the notice itself or accessed from a hyperlink in the notice.

Figure 4:
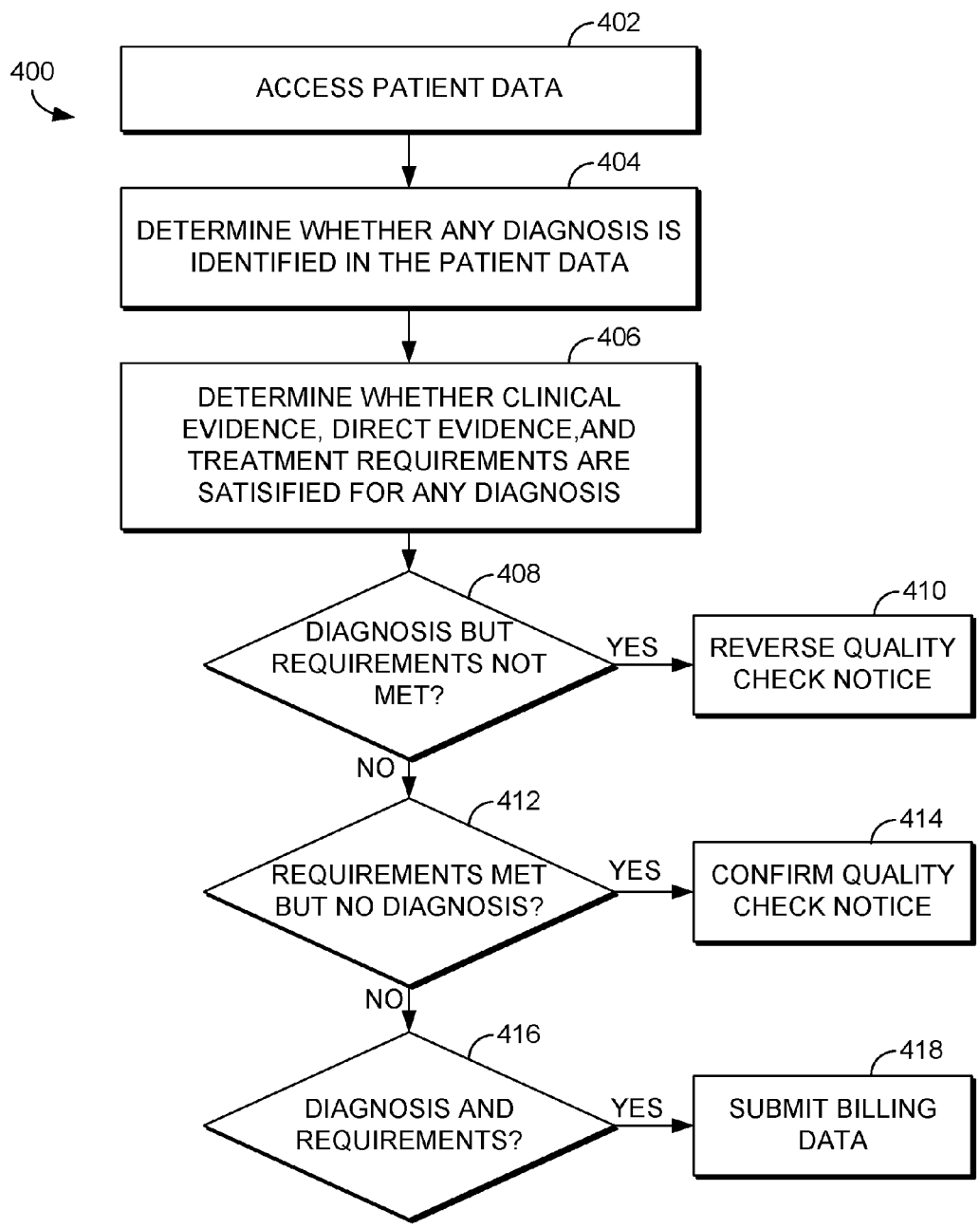
FIG. 4 is a flow diagram showing a method for performing reverse quality checks and forward quality checks in accordance with an embodiment of the present invention.

Turning now to FIG. 4, a flow diagram is provided illustrating a method for performing reverse quality checks and confirmation quality checks in accordance with an embodiment of the present invention. As shown at block 402, patient data is accessed. The patient data may be accessed, for instance, from an electronic medical record for the patient.

The patient data is analyzed to determine whether there is any diagnosis identified in the patient data that impacts quality and/or payments for the services rendered to the patient, as shown at block 404. For instance, the system may store a list of diagnoses that impact quality and/or payments. This may include, for instance, diagnoses that fall into different DRGs for Medicare payments. As such, the system may determine the patient data includes one of the listed diagnoses.

The patient data is also analyzed to determine whether clinical evidence, direct evidences, and treatment requirements are satisfied for any diagnosis, as shown at block 406. In some embodiments, this includes iterating through the requirements for each diagnosis for which requirements are defined and stored by the system and determining whether the patient data satisfies all requirements for any of the diagnoses. In other embodiments, determination may be made without iterating through each diagnosis. This may be done, for instance, by analyzing the patient data to categorize portions of the patient data as clinical evidence, direct evidence, or treatments, and then using the categorized patient data to determine if all requirements for any diagnosis are satisfied (e.g., using data structures, such as reverse indexes or tree-like graphs, as discussed above).

If a diagnosis is identified from the patient data but the patient data doesn't support the clinical evidence, direct evidence, and treatment requirements for that diagnosis as shown at block 408, a reverse quality check notice is generated and provided to a clinician, as shown at block 410. Alternatively, if the patient data supports the clinical evidence, direct evidence, and treatment requirements for a diagnosis but the diagnosis has not been confirmed by a physician as shown at block 412, a confirmation quality check notice is generated and provided to the clinician, as shown at block 414. Finally, if a diagnosis is identified in the patient data and the patient data supports the clinical evidence, direct evidence, and treatment requirements for the diagnosis as shown at block 416, billing data is submitted, as shown at block 418.

Figure 5:
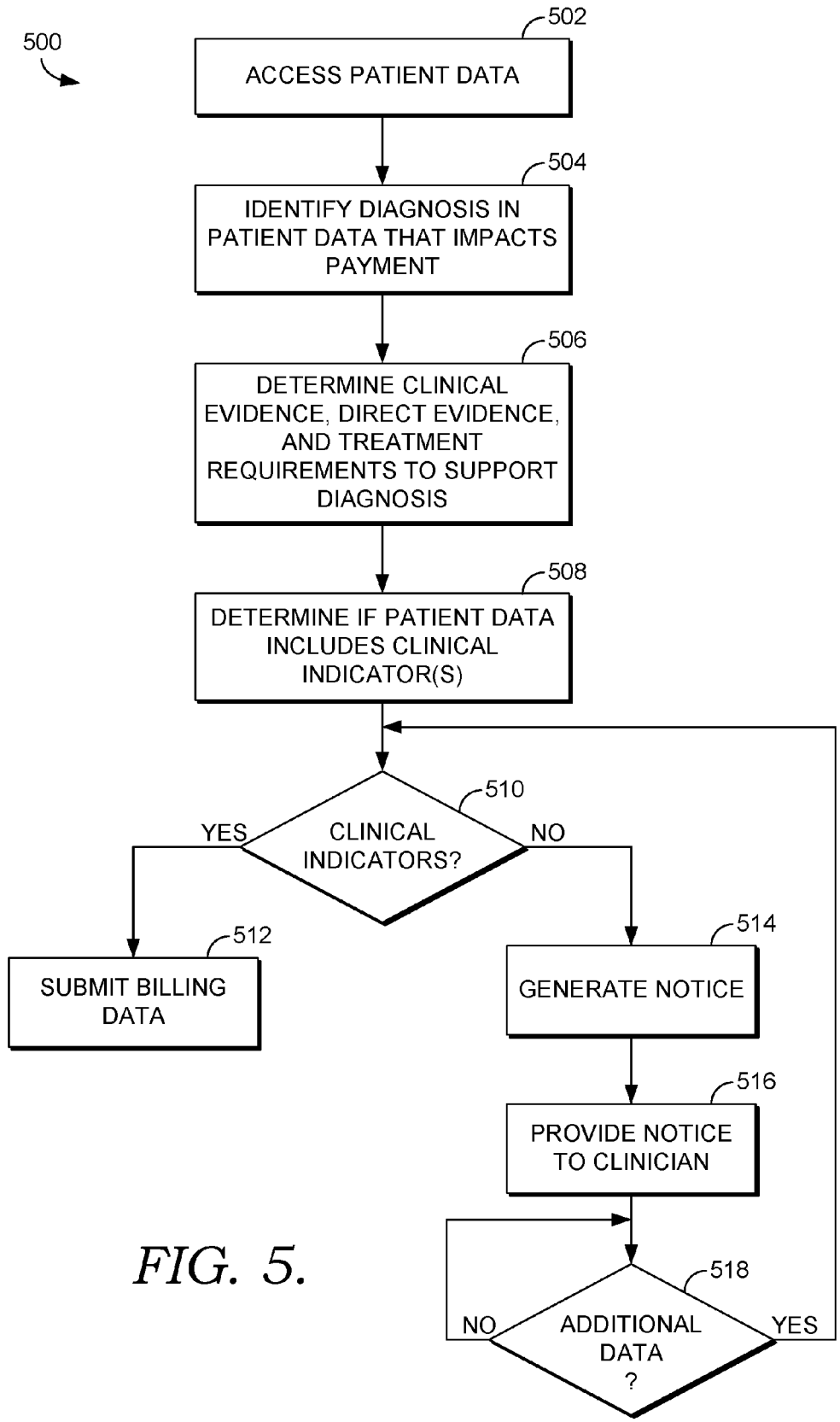
FIG. 5 is a flow diagram showing a method for performing a reverse quality check in accordance with an embodiment of the present invention.

Turning to FIG. 5, a flow diagram is provided that illustrates a method 500 for performing reverse quality checks in accordance with an embodiment of the present invention. As shown at block 502, patient data is accessed. The patient data is analyzed to identify a diagnosis in the patient data that impacts quality and/or payment for the services rendered to the patient, as shown at block 504. For instance, the system may store a list of diagnoses that impact quality and/or payments. This may include, for instance, diagnoses that fall into different DRGs for Medicare payments. As such, the system may determine the patient data includes one of the listed diagnoses.

The clinical evidence, direct evidence, and treatment requirements to support the diagnosis identified in the patient data are determined, as shown at block 506. For instance, the system may store information regarding requirements to support each diagnosis that impacts quality and/or payment for rendered services. Accordingly, the system may use this information to look up the clinical evidence, direct evidence, and treatment requirements needed to support the diagnosis identified in the patient data.

A determination is made at block 508 regarding whether the patient data available for the patient includes the clinical indicators (i.e., clinical evidence, direct evidence, and treatment(s)) required to support the identified diagnosis. If it is determined at block 510 that the patient data includes the required clinical indicators, billing data is submitted to a payment provider, as shown at block 512.

Alternatively, if it is determined at block 510 that the patient data does not include all the required clinical indicators, a notice is generated at block 514 and provided to a clinician, as shown at block 516. The notice may be provided to any number of clinicians and any of a variety of different types of clinicians. For instance, the notice may be provided to a CDI specialist and/or to a treating physician.

The notice may provide a variety of different information in various embodiments of the present invention. In some embodiments, the notice simply indicates that a diagnosis that impacts payment was identified as being confirmed by a physician but all clinical indicators required to support the diagnosis have not been found in available patient data. In other embodiments, the notice identifies which clinical indicators are missing from the patient data. In some embodiments, the notice identifies clinical indicators that were found in the patient data. In further embodiments, the notice identifies particular data that is needed to satisfy the missing clinical indicators or other actions that may be taken to collect the needed data. In some embodiments, the notice provides a user interface to collect, from a clinician, additional information or clarifying information that is added to the patient data to facilitate billing. The user interface may be a part of the notice itself or accessed from a hyperlink in the notice. In further embodiments, the notice includes one or more hyperlinks to perform specific actions (e.g., submit orders for tests) to collect needed data. Accordingly, the notice may prompt a clinician to perform additional actions to collect data needed to show clinical indicators required to support a diagnosis are present.

After the notice is sent to a clinician, the system monitors whether additional data is received for the patient, as shown at block 518. As shown in FIG. 5, the system may periodically or continuously check to see if new data is received until new patient data is available or some other point in time, such as a time at which the billing information is to be submitted to a payment provider. Alternatively, if new patient data is detected at block 516, the process of determining whether the patient data includes the clinical indicators required to support the diagnosis may be repeated, as shown by the return to block 510.

Figure 6:
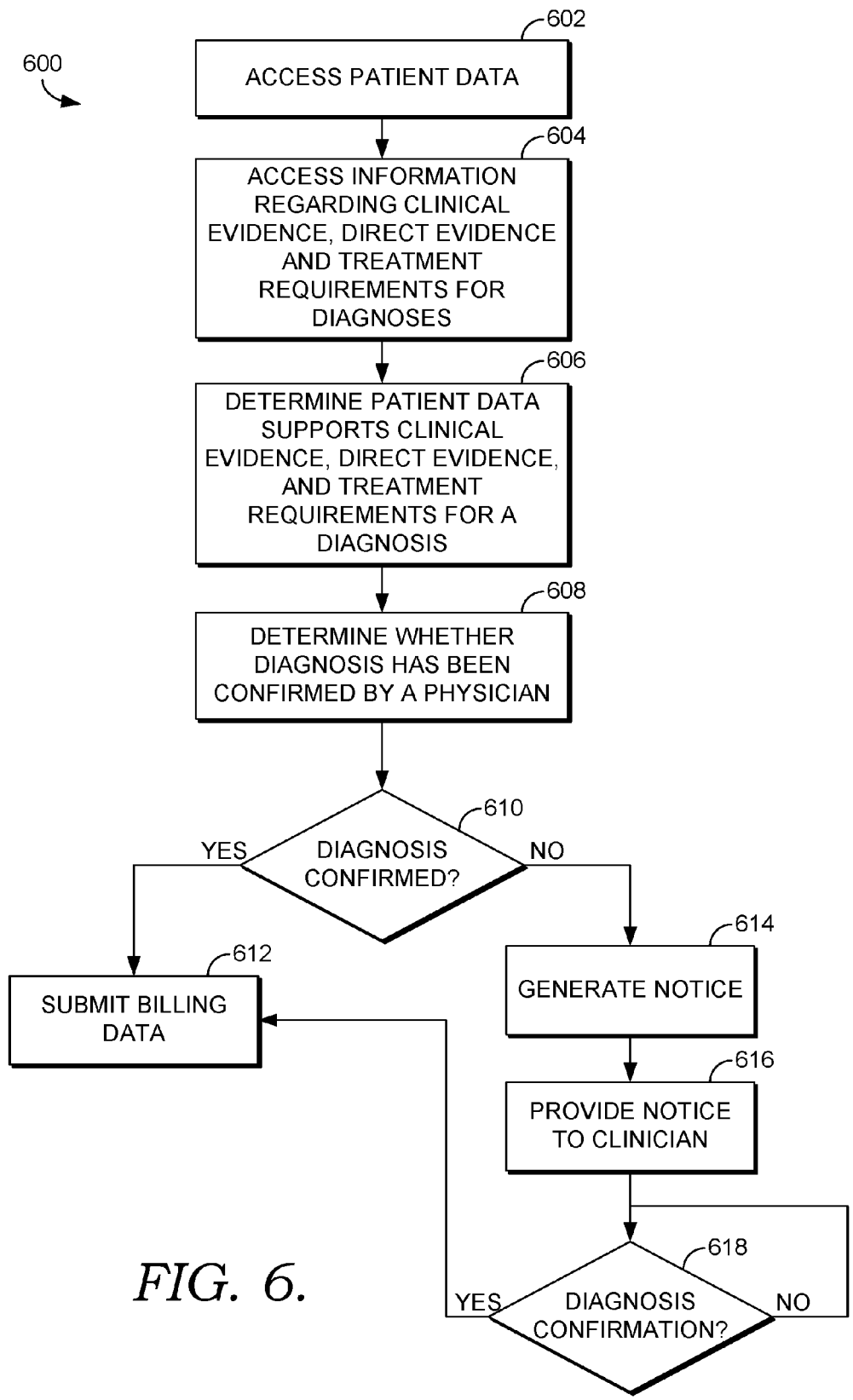
FIG. 6 is a flow diagram showing a method for performing a confirmation quality check in accordance with an embodiment of the present invention.

With reference now to FIG. 6, a flow diagram is provided that illustrates a method 600 for performing confirmation quality checks in accordance with an embodiment of the present invention. As shown at block 602, patient data is accessed. Information regarding clinical evidence, direct evidence, and treatment requirements for a number of diagnoses are accessed, as shown at block 604. As previously discussed, requirements for diagnoses may be stored, for instance, in data structures indexed by diagnosis and/or requirements and/or graph-like structures may be employed. The patient data is analyzed to determine that the clinical evidence, direct evidence, and treatment requirements are all satisfied for a diagnosis, as shown at block 606.

A determination is made at block 608 regarding whether the diagnosis identified at block 606 has been confirmed by a physician. If it is determined at block 610 that the diagnosis has been confirmed by a physician, billing data is submitted to a payment provider, as shown at block 612.

Alternatively, if it is determined at block 610 that the diagnosis has not been confirmed by a physician, a notice is generated at block 614 and provided to a clinician, as shown at block 616. The notice may be provided to any number of clinicians and any of a variety of different types of clinicians. For instance, the notice may be provided to a CDI specialist or a treating physician.

The notice may provide a variety of different information in various embodiments of the present invention. In some embodiments, the notice indicates that the quality indicator requirements for a diagnosis that impacts payment were identified, but the diagnosis has not been confirmed by a clinician. The notice may include or exclude information regarding the clinical evidence, direct evidence, and treatments from the patient data used to determine the clinical indicator requirements for the diagnosis are supported. In some embodiments, the notice provides a user interface to collect, from a clinician, a confirmation of a diagnosis and/or other information. The user interface may be a part of the notice itself or accessed from a hyperlink in the notice.

After the notice is sent to a clinician, the system monitors whether a confirmation of the diagnosis is received, as shown at block 618. As shown in FIG. 6, the system may periodically or continuously check to see if new data is received until the diagnosis confirmation is made or some other point in time, such as a time at which the billing information is to be submitted to a payment provider. Alternatively, if a diagnosis confirmation is detected at block 616, billing data is submitted to a payment provider, as shown at block 612.

As can be understood, embodiments of the present invention provide a system that may be employed by a hospital to perform reverse quality checks and confirmation quality checks. The present invention has been described in relation to particular embodiments, which are intended in all respects to be illustrative rather than restrictive. Alternative embodiments will become apparent to those of ordinary skill in the art to which the present invention pertains without departing from its scope.

From the foregoing, it will be seen that this invention is one well adapted to attain all the ends and objects set forth above, together with other advantages which are obvious and inherent to the system and method. It will be understood that certain features and subcombinations are of utility and may be employed without reference to other features and subcombinations. This is contemplated and within the scope of the claims.

What is claimed is:

1. A method for improving clinical diagnostic accuracy, the method comprising:
   providing an application for installation on a clinician computing device associated with a clinician;
   accessing patient data from an electronic medical record for a patient;
   determining whether any of a plurality of diagnoses that impact payment for medical services rendered for the patient are confirmed by a physician in the patient data;
   determining whether clinical evidence, direct evidence, and treatment requirements for any of the plurality of diagnoses are satisfied by the patient data;
   if a first diagnosis has been confirmed by the physician but at least one of the clinical evidence, direct evidence, and treatment requirements for the first diagnosis is not satisfied by the patient data, generating a first electronic message providing a reverse quality check notification, wherein the reverse quality check notification comprises a user interface that prompts and allows the physician to enter information to satisfy at least one of the clinical evidence, direct evidence, and treatment requirements for first diagnosis, wherein the first electronic message causes the application to display the reverse quality check notification on the clinician computing device; and
   if the clinical evidence, direct evidence, and treatment requirements for a second diagnosis are satisfied by the patient data but the second diagnosis has not been confirmed by the physician, generating a second electronic message providing a confirmation quality check notification, wherein the confirmation quality check notification comprises a user interface that prompts and allows the physician to confirm the second diagnosis, wherein the second electronic message causes the application to display the confirmation quality check notification on the clinician computing device.

2. The method of claim 1, wherein the payment for the medical services rendered for the patient is based on a diagnosis-related group (DRG) payment system.

3. The method of claim 2, wherein the diagnosis affects classification into a DRG used to determine the payment for the medical services rendered for the patient.

4. The method of claim 1, wherein the first electronic message includes a hyperlink to access a user interface to provide data for the at least one of the clinical evidence, direct evidence, and treatment requirements to support the first diagnosis.

5. The method of claim 4, wherein the method further comprises:
   receiving, via the user interface, the data for the at least one of the clinical evidence, direct evidence, and treatment requirements to support the first diagnosis; and
   submitting billing data based on the first diagnosis.

6. The method of claim 1, wherein the second electronic message includes a hyperlink to access a user interface to confirm the first diagnosis for the patient.

7. The method of claim 6, wherein the method further comprises:
   receiving, via the user interface, a confirmation of the second diagnosis for the patient; and
   submitting billing data based on the second diagnosis.

8. The method of claim 1, wherein the clinician comprises the physician.

9. One or more computer storage media storing computer-useable instructions that, when used by one or more computing devices, cause the one or more computing devices to perform operations comprising:
   providing an application for installation on a clinician computing device associated with a clinician;
   identifying, from electronic medical data storing patient data for a patient, a diagnosis that impacts payment for medical services rendered for the patient;
   accessing a data store storing requirements to support the diagnosis;
   determining, from the data store, clinical evidence, direct evidence, and treatment requirements to support the diagnosis;
   determining that at least one of the clinical evidence, direct evidence, and treatment requirements to support the diagnosis is not present in the patient data;
   generating an electronic message by inserting, into the electronic message, at least a portion of the patient data and information identifying the at least one of the clinical evidence, direct evidence, and treatment requirements to support the diagnosis that is not present in the patient data; and
   providing the electronic message, over a communication network, to the clinician computing device associated with a clinician, wherein the electronic message comprises electronic message causes the application to display a user interface that prompts and allows the physician to enter information to satisfy at least one of the clinical evidence, direct evidence, and treatment requirements for first diagnosis.

10. The one or more computer storage media of claim 9, wherein the operations further comprise:
    preventing submission of billing data for the patient that includes the diagnosis in response to determining that the at least one of the clinical evidence, direct evidence, and treatment requirements to support the diagnosis is not present in the patient data.

11. The one or more computer storage media of claim 9, wherein generating the electronic message comprises including a hyperlink to access a user interface to provide data for the at least one of the clinical evidence, direct evidence, and treatment requirements to support the diagnosis that is not present in the patient data.

12. The one or more computer storage media of claim 11, wherein the electronic message indicates a clinical action required to the data for the at least one of the clinical evidence, direct evidence, and treatment requirements to support the diagnosis that is not present in the patient data, and wherein the user interface allows for placement of a clinical order for the clinical action.

13. The one or more computer storage media of claim 11, wherein the operations further comprise:
    receiving, via the user interface, the data for the at least one of the clinical evidence, direct evidence, and treatment requirements to support the diagnosis that is not present in the patient data; and
    submitting billing data that includes the diagnosis and a collection of data for the clinical evidence, direct evidence, and treatment requirements to support the diagnosis.

14. The one or more computer storage media of claim 9, wherein generating the electronic message comprises including information identifying at least one other of the clinical evidence, direct evidence, and treatment requirements to support the diagnosis that is present in the patient data.

15. The one or more computer storage media of claim 9, wherein generating the electronic message comprises retrieving supplemental evidence relevant to the first diagnosis and including information regarding the supplemental evidence in the electronic message.

16. A system for improving the accuracy of a clinical diagnosis, the system comprising:
   one or more processors; and
   one or more computer storage media storing instructions that, when used by the one or more processors, cause the one or more processors to:
   provide an application for installation on a clinician computing device associated with a clinician;
   determine that a clinician has signed a document confirming a first diagnosis for a patient;
   in response to the confirming the first diagnosis, access electronic medical data storing patient data for the patient;
   determining, from the data store, clinical evidence, direct evidence, and treatment requirements to support the diagnosis;
   determine that at least one of the clinical evidence, direct evidence, and treatment requirements for the first diagnosis is not satisfied by the patient data;
   generate an electronic message that identifies the at least one of the clinical evidence, direct evidence, and treatment requirements to support the diagnosis is not present in the patient data;
   provide the electronic message, over a communication network, to the clinician computing device, wherein the electronic message causes the application to display includes a user interface that prompts and allows the clinician to enter information to satisfy at least one of the clinical evidence, direct evidence, and treatment requirements for the first diagnosis.

17. The system of claim 16, wherein the electronic message is generated by including a hyperlink to access a user interface to confirm the first diagnosis for the patient.

18. The system of claim 17, wherein the instructions further cause the one or more processors to:
   receive, via the user interface, a confirmation of the first diagnosis for the patient; and
   submit billing data that includes the first diagnosis and a collection of data for the clinical evidence, direct evidence, and treatment requirements to support the diagnosis.

19. The system of claim 16, wherein the patient data is analyzed to determine if the patient data supports the clinical evidence, direct evidence, and treatment requirements for each of the plurality of diagnoses that impact payment for rendered medical services.

20. The system of claim 16, wherein the electronic message is generated by including information identifying patient data satisfying the clinical evidence, direct evidence, and treatment requirements to support the diagnosis.

* * * * *